United States Patent
Park et al.

(10) Patent No.: US 10,842,734 B2
(45) Date of Patent: Nov. 24, 2020

(54) DAHLIA PINNATA COMPOSITION, DAHLIA PINNATA COMPOSITION POWDER, COSMETIC COMPOSITION, AND PRODUCING METHOD THEREFOR

(71) Applicant: BARAM INTERNATIONAL CO., LTD., Seoul (KR)

(72) Inventors: Rae Hyun Park, Seoul (KR); Han Na Jo, Changwon-Si (KR); Keong A Ryu, Busan (KR); Dong Jin Jang, Gimhae-Si (KR); Sung Tae Kim, Seoul (KR)

(73) Assignee: BARAM INTERNATIONAL CO., LTD., Seoul (KR)

( * ) Notice: Subject to any disclaimer, the term of this patent is extended or adjusted under 35 U.S.C. 154(b) by 0 days.

(21) Appl. No.: 16/762,073

(22) PCT Filed: Nov. 13, 2018

(86) PCT No.: PCT/KR2018/013754
§ 371 (c)(1),
(2) Date: May 6, 2020

(87) PCT Pub. No.: WO2019/146889
PCT Pub. Date: Aug. 1, 2019

(65) Prior Publication Data
US 2020/0337986 A1     Oct. 29, 2020

(30) Foreign Application Priority Data

Jan. 24, 2018   (KR) ........................ 10-2018-0008715

(51) Int. Cl.
*A61K 36/28*     (2006.01)
*A61K 8/9789*    (2017.01)
(Continued)

(52) U.S. Cl.
CPC ............ *A61K 8/9789* (2017.08); *A61K 8/022* (2013.01); *A61K 8/347* (2013.01); *A61Q 19/08* (2013.01);
(Continued)

(58) Field of Classification Search
CPC ...................................................... A61K 36/28
See application file for complete search history.

(56) References Cited

FOREIGN PATENT DOCUMENTS

| JP | 2008-247839 A | 10/2008 |
|----|---------------|---------|
| JP | 2008-308436 A | 12/2008 |

(Continued)

OTHER PUBLICATIONS

International Search Report for PCT/KR2018/013754 dated Apr. 22, 2019 [PCT/ISA/210].

(Continued)

*Primary Examiner* — Rosanne Kosson
(74) *Attorney, Agent, or Firm* — Sughrue Mion, PLLC

(57) ABSTRACT

Disclosed a *Dahlia pinnata* composition, *Dahlia pinnata* composition powders, a *Dahlia pinnata* cosmetic composition and a method for producing the same. A method for producing a *Dahlia pinnata* composition includes preparing *Dahlia pinnata* petals; adding and stirring ethanol into the *Dahlia pinnata* petals to extract *Dahlia pinnata* extract; filtering the *Dahlia pinnata* extract; and diluting the filtered *Dahlia pinnata* extract in a solvent to obtain a *Dahlia pinnata* composition having an antioxidant efficacy. The *Dahlia pinnata* composition is produced by the method for producing a *Dahlia pinnata* composition, and thus has an antioxidant efficacy. In addition, the cosmetic composition includes the *Dahlia pinnata* extract and thus has an antioxidant efficacy.

8 Claims, 2 Drawing Sheets

(51) Int. Cl.
    *A61K 8/02*     (2006.01)
    *A61Q 19/08*    (2006.01)
    *A61K 8/34*     (2006.01)
(52) U.S. Cl.
    CPC .... *A61K 2800/522* (2013.01); *A61K 2800/84* (2013.01)

(56) References Cited

FOREIGN PATENT DOCUMENTS

| KR | 10-2002-0086326 A | 11/2002 | |
| KR | 10-2006-0100115 A | 9/2006 | |
| KR | 10-2017-0122671 A | 11/2017 | |
| WO | WO-2010146788 A1 * | 12/2010 | ........... A61K 9/0014 |

OTHER PUBLICATIONS

Written Opinion for PCT/KR2018/013754 dated Apr. 22, 2019 [PCT/ISA/237].

Korean Notice of Allowance for Korean Patent Application No. 10-2018-0008715 dated Nov. 2, 2018.

Office Action dated Sep. 25, 2020 in Chinese Application No. 201880071663.9.

Lara-Cortes et al., "Antioxidant Capacity, Nutritional and Functional Composition of Edible Dahlia Flowers", Revista Chapingo Serie Horticultura, 2014, vol. 20, No. 1, pp. 101-116 (16 pages total).

* cited by examiner

DAHLIA PINNATA COMPOSITION, DAHLIA PINNATA COMPOSITION POWDER, COSMETIC COMPOSITION, AND PRODUCING METHOD THEREFOR

CROSS REFERENCE TO RELATED APPLICATIONS

This application is a National Stage of International Application No. PCT/KR2018/013754 filed Nov. 13, 2018, claiming priority based on Korean Patent Application No. 10-2018-0008715, filed Jan. 24, 2018.

TECHNICAL FIELD

The present disclosure relates to a *Dahlia pinnata* composition, *Dahlia pinnata* composition powders, a *Dahlia pinnata* cosmetic composition and a method for producing the same. More particularly, the present disclosure relates to a *Dahlia pinnata* composition, *Dahlia pinnata* composition powders, a *Dahlia pinnata* cosmetic composition, each having an extract of an effective ingredient from *Dahlia pinnata* petal having antioxidant effect, and a method for producing the same.

BACKGROUND ART

In a process of energy production in a body, water, carbon dioxide and oxygen are generated. This oxygen is called free radical (reactive oxygen). This reactive oxygen performs an immune function and signal transduction function in the body. However, an excessively large amount of the reactive oxygen may cause aging and diseases. The excessive amount of the reactive oxygen may cause oxidative damage to various constituents (lipids, proteins, nucleic acids) in cells. In particular, a skin exposed to the outside may be continuously affected by the oxidative damage, thereby leading to the skin aging. Thus, such reactive oxygen is considered to be an important factor of the skin aging.

A typical method to minimize the oxidative damage caused by the reactive oxygen and the resulting aging process is to intake physiologically active substances (e.g., vitamins, flavonoids, phenolic compounds, etc.) having antioxidant effect.

In order to minimize the oxidative damage, not only such a physiologically active substance alone is digested, but also, a natural substance containing the same is digested. Thus, researches on extracting of natural antioxidant materials that maintain the antioxidant system in the body from natural materials are being actively carried out. Plants have a variety of secondary metabolites, which exhibit antioxidant activity and may be obtained from a variety of extracts. Because the secondary metabolites are natural materials, the secondary metabolites have an advantage that the secondary metabolites may be used relatively safely compared with a synthetic material.

These natural antioxidant materials with antioxidant activity are applied throughout the industry and are ingested into the body through a variety of routes. In typical examples, the natural antioxidant materials are applied to foods and cosmetics, which are ingested into and applied onto the body, thereby reducing the oxidative damage and preventing the aging.

Meanwhile, *Dahlia pinnata* is a perennial plant of dicotyledoneae Campanulales Asteraceae. *Dahlia pinnata* is a plant with features of tubers and herbs and is originated from Mexico. *Dahlia pinnata* is cultivated widely in various countries for ornamental use. *Dahlia pinnata* reproduces using sweet potato-like roots. The trunk of *Dahlia pinnata* is cylindrical, with many branches, no hairs, green and 1.5 to 2 m height. Leaves thereof are grown opposite to each other and split 1-2 times. The small leaf of *Dahlia pinnata* is ovate, with serrate on the edge, with a front face of the leaf being dark green, with a back face being white, and with the petiole having few wings.

Roots of *Dahlia pinnata* have analgesic effect against dental pain caused by tooth decay. In addition, *Dahlia pinnata* petal is effective for diseases such as cardiovascular disease, dementia and cancer. Such a *Dahlia pinnata* petal-extract based composition may be used as a raw material for medicines for diseases such as cardiovascular diseases, dementia and cancer.

A conventional document relating to an antioxidant active cosmetic composition using natural antioxidant materials may include Korean Patent Application No. 20020047048 titled "Cosmetic composition comprising extract of *Rosa multiflora* with antioxidative activity and preparation method of the extract", Korean Patent Application No. 20080107420 titled "Protective effects of *Eucommia ulmoides* on UVB-induced oxidative stress in human keratinocytes", and Korean Patent Application No. 20050021778 tilted "Cosmetic composition including *Nelumbo nucifera* extract with antioxidant effect". However, all of the above documents fail to disclose an antioxidant activity composition including the above-described *Dahlia pinnata* extract as a major component.

DISCLOSURE

Technical Goals

A purpose of embodiments of the present disclosure is to provide a *Dahlia pinnata* composition, *Dahlia pinnata* composition powders, a *Dahlia pinnata* cosmetic composition, each having an extract of an effective ingredient from *Dahlia pinnata* petal having antioxidant effect, and a method for producing the same.

Further, another purpose of embodiments of the present disclosure is to provide a *Dahlia pinnata* composition, *Dahlia pinnata* composition powders, a *Dahlia pinnata* cosmetic composition, each being added to foods or cosmetics, and imposing antioxidant effects to the foods or cosmetics and providing anti-aging effects, and a method for producing the same.

Technical Solutions

A cosmetic composition according to an embodiment will be described.

The cosmetic composition including *Dahlia pinnata* extract may have an antioxidant efficacy.

According to one aspect, the cosmetic composition may have a content of *Dahlia pinnata* extract ranging from 16 μg/ml to 20000 μg/ml. More preferably, the content of *Dahlia pinnata* extract may be in a range of from 500 μg/ml to 10000 μg/ml.

A method for producing a *Dahlia pinnata* composition according to an embodiment will be described.

The method for producing the *Dahlia pinnata* composition may include: preparing *Dahlia pinnata* petals; adding and stirring ethanol into the *Dahlia pinnata* petals to extract *Dahlia pinnata* extract; filtering the *Dahlia pinnata* extract;

and diluting the filtered *Dahlia pinnata* extract in a solvent to obtain a *Dahlia pinnata* composition having an antioxidant efficacy.

According to one aspect, in extracting the *Dahlia pinnata* extract, 5 to 20 ml of ethanol may be added per 1 g of the *Dahlia pinnata* petal to extract the *Dahlia pinnata* extract.

According to one aspect, the *Dahlia pinnata* composition may have a phenolic compound content of 43.1 µg/100 mg to 56.5 µg/100 mg.

According to one aspect, the *Dahlia pinnata* composition may have a content of the *Dahlia pinnata* extract ranging from 16 µg/ml to 20000 µg/ml.

According to one aspect, the *Dahlia pinnata* composition may have a content of the *Dahlia pinnata* extract of 500 µg/ml to 10000 µg/ml.

According to one aspect, the *Dahlia pinnata* composition may have an ability of an antioxidant component to remove 85% to 89% of DPPH (2,2-diphenyl-1-picrylhydrazyl) free radicals.

According to one aspect, the *Dahlia pinnata* composition may have a content of the *Dahlia pinnata* extract ranging from 16 µg/ml to 400 µg/ml.

According to one aspect, the *Dahlia pinnata* composition may have inhibition of 71.7% to 105.6% of superoxide dismutase activity.

According to one aspect, filtering the *Dahlia pinnata* extract may include filtering the *Dahlia pinnata* extract with a syringe filter.

A method for producing *Dahlia pinnata* composition powders according to an embodiment will be described.

The method for producing *Dahlia pinnata* composition powders includes lyophilizing the *Dahlia pinnata* composition prepared by the above-described method; and converting the lyophilized *Dahlia pinnata* composition into powders form.

The *Dahlia pinnata* composition and *Dahlia pinnata* composition powders having antioxidative effects may be prepared by the above-described preparation method.

In addition, a cosmetic composition having antioxidant activity including the *Dahlia pinnata* composition prepared by the above-described preparation method may be prepared.

Advantageous Effects

The *Dahlia pinnata* composition prepared by extracting the effective ingredient from the *Dahlia pinnata* petal may be converted into a liquid or powders form, which may be easily added to food or cosmetics.

In addition, the antioxidant effect may be exhibited from the food or cosmetic having the *Dahlia pinnata* composition, thereby to provide the anti-aging efficacy.

BEST MODE FOR CARRYING OUT THE INVENTION

Figure 1:
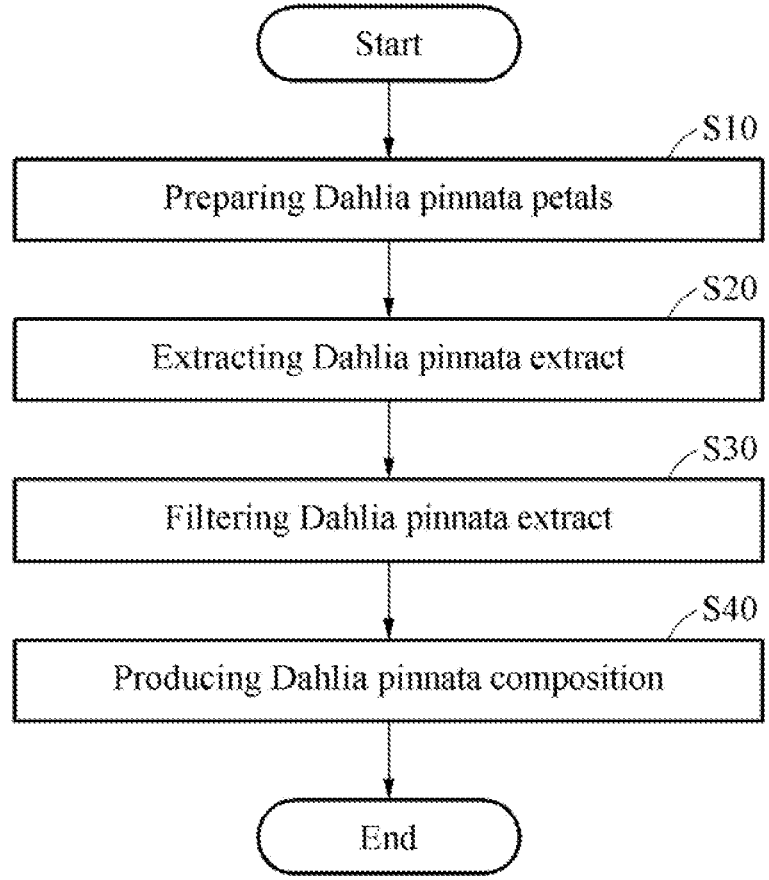
FIG. 1 is a flowchart of the method for producing the *Dahlia pinnata* composition according to an embodiment.

Examples of various embodiments are illustrated and described further below with reference to the drawings. The same reference numbers in different figures denote the same or similar elements, and as such perform similar functionality. In other instances, well-known methods, procedures, components, and circuits have not been described in detail so as not to unnecessarily obscure aspects of the present disclosure.

It will be understood that, although the terms "first", "second", "third", A, B, (a), (b) and so on may be used herein to describe various elements, these elements should not be limited by these terms. These terms are used to distinguish one element from another element. It will be understood that when an element is referred to as being "connected to", or "coupled to" or "accessed to" another element, it can be directly on, connected to, or coupled to, or accessed to the other element, or one or more intervening elements may be present.

Components included in one embodiment may have the same name as a component having the same function in other embodiments. Unless otherwise stated, a description of one embodiment may be applied to other embodiments. A detailed description of overlapping portions between embodiments will be omitted.

Prior to describing this embodiment, *Dahlia pinnata* extract means *Dahlia pinnata* petal component extracted by adding ethanol to *Dahlia pinnata* petal. *Dahlia pinnata* composition means a solvent including *Dahlia pinnata* extract. Further, a content (µg/ml) of *Dahlia pinnata* extract means the number of µg of *Dahlia pinnata* extract dissolved in 1 ml of *Dahlia pinnata* composition, that is, a solvent including *Dahlia pinnata* extract.

Further, the cosmetic composition means a cosmetic material including *Dahlia pinnata* extract. The cosmetic material means a combination of additives or additives for producing cosmetics, the additives or additives being free of the *Dahlia pinnata* extract.

The *Dahlia pinnata* petal includes a phenolic compound that inhibits oxidative damage by reactive oxygen and the progression of aging caused by the damage. Therefore, the *Dahlia pinnata* flower composition including the *Dahlia pinnata* petal extract has an antioxidant efficacy, which inhibits oxidative damage and progression of the aging. Such a *Dahlia pinnata* flower composition may have an antioxidant effect and thus may provide an antioxidant efficacy to the user when the composition is provided in the food or cosmetics form to the user. Further, *Dahlia pinnata* petals have different colors depending on the type. The composition including the *Dahlia pinnata* petal extracts may have different colors. This may easy to add colors in the food or cosmetics.

The *Dahlia pinnata* petal extract may be added to cosmetics of various cosmetics such as cleansing cosmetics, basic cosmetics, color cosmetics, hair cosmetics, and functional cosmetics. Thus, the cosmetics may have antioxidant activity functions such as whitening and wrinkle improvement. Further, the cosmetic composition including the *Dahlia pinnata* extract has a color depending on the color of the petal. Thus, the cosmetic composition including the *Dahlia pinnata* extract may be used as a natural pigment for cosmetics such as makeup base, foundation, lipstick, eye shadow, and manicure.

Hereinafter, a method for producing a *Dahlia pinnata* flower composition according to an embodiment will be described.

FIG. 1 is a flowchart of the method for producing the *Dahlia pinnata* composition according to an embodiment.

Referring to FIG. 1, the method for producing a *Dahlia pinnata* composition may include preparing *Dahlia pinna* petals (S10); extracting a *Dahlia pinnata* extract (S20); filtering the *Dahlia pinnata* extract (S30); and producing a *Dahlia pinnata* composition (S40).

The step (S10) of preparing the *Dahlia pinnata* petals may include a step of preparing the *Dahlia pinnata* petal which has been cleaned of foreign matters and washed. For example, the foreign matter has been removed from the *Dahlia pinnata* petal which in turn has washed. Thus, 20 g of the petal may be prepared. However, this is only an example. The amount of *Dahlia pinnata* composition may be varied depending on the content of the *Dahlia pinnata* composition being produced.

The step (S20) of extracting the *Dahlia pinnata* extract may include adding ethanol to the prepared *Dahlia pinnata* petals and stirring the mixture to extract the *Dahlia pinnata* extract including the antioxidant component. In this connection, this step may extract the *Dahlia pinnata* extract by adding 5 to 20 ml of ethanol per 1 g of the *Dahlia pinnata* petal. In a more preferred example, 10 ml of ethanol may be added per 1 g of the *Dahlia pinnata* petal to extract the *Dahlia pinnata* extract. For example, 200 ml of ethanol may be added to 20 g of *Dahlia pinnata* petal. Then, the *Dahlia pinnata* extract may be extracted by stirring the mixture at a room temperature for 5 hours at a speed of 30 rpm.

The extraction of *Dahlia pinnata* flowers by distillation or squeezing may destroy effective components. Therefore, in the step of extracting the *Dahlia pinnata* extract, the ethanol may be added to extract the *Dahlia pinnata* petal extract. When the *Dahlia pinnata* petals are immersed in the ethanol, the effective component from the petals is completely dissolved into ethanol, and, thus, the solvent is vaporized away to obtain the extract only. In this way, the *Dahlia pinnata* extract can be extracted so that the effective ingredients included in the flower are not destroyed. In addition to the extraction method using the ethanol, the *Dahlia pinnata* flower extract can be extracted with volatile organic solvents such as petroleum ether, benzine, chloroform, etc. However, in the method using the volatile organic solvents, the toxicity may remain due to the residual organic solvents. Thus, the latter method is not suitable for producing the *Dahlia pinnata* compositions used in food or cosmetics.

The step (S30) of filtering the *Dahlia pinnata* extract may filter the *Dahlia pinnata* extract with a filter and store the filtered extract at a temperature of 4° C. For example, the *Dahlia pinnata* extract may be filtered through a 25 mm syringe filter (HM) and stored in a refrigerator at 4° C.

In this connection, a syringe filter is a disposable filter used to filter suspended matter in a liquid sample. The syringe filter may include a membrane filter that separates the mixture by separating and passing certain components therethrough. The syringe filter may be attached to the tip of the syringe. Then, a small amount of pressure is applied to the syringe, the extract may be filtered through the membrane filter.

However, the syringe filter is just an example. Various filters that can filter the *Dahlia pinnata* extract may be employed.

The step (S40) of producing the *Dahlia pinnata* composition may produce the *Dahlia pinnata* composition by diluting the filtered *Dahlia pinnata* extract in a solvent to adjust the content of the *Dahlia pinnata* extract. For example, ethanol may be used as a solvent in the step (S40) of producing the *Dahlia pinnata* composition. The *Dahlia pinnata* composition may be produced at a content of 100,000 μg/ml of the *Dahlia pinnata* extract relative to the solvent. Depending on the applications of the *Dahlia pinnata* composition, the extract may be diluted via the addition of the ethanol thereto. For example, the *Dahlia pinnata* composition may have a content 16 μg/ml to 20000 μg/ml of the *Dahlia pinnata* extract relative to the solvent. The *Dahlia pinnata* composition may be adjusted depending on the intended use thereof at a content ranging from 16 μg/ml to 20000 μg/ml of the *Dahlia pinnata* extract relative to the solvent.

For example, the *Dahlia pinnata* composition may have a content of 500 μg/ml to 20000 μg/ml of the *Dahlia pinnata* extract relative to the solvent. In this case, the *Dahlia pinnata* composition may have a DPPH free radical removal capability of 85% to 89% by the antioxidant component. As another example, the *Dahlia pinnata* composition may have a content of 16 μg/ml to 400 μg/ml of the *Dahlia pinnata* extract relative to the solvent. In this case, the *Dahlia pinnata* composition may have an inhibition rate of 67.8% to 105.6% of the superoxide dismutase activity.

As a more preferred example, the *Dahlia pinnata* composition may have a content of 500 μg/ml to 10000 μg/ml of *Dahlia pinnata* extract relative to the solvent. The *Dahlia pinnata* composition shows a high antioxidative activity when the content of *Dahlia pinnata* extract relative to the solvent is in a range of 500 μg/ml to 10000 μg/ml.

Such a *Dahlia pinnata* composition may be added to the food in the form of a liquid and may be indigested. Such a *Dahlia pinnata* composition may be added to the cosmetic in the form of a liquid. In other words, the *Dahlia pinnata* composition may be composed of the diluted *Dahlia pinnata* extract in the ethanol. Then, the cosmetic or food composition may be produced by adding the *Dahlia pinnata* composition to the cosmetic or food products.

In another example, the solvent may be the cosmetic material. In this case, a cosmetic composition including the *Dahlia pinnata* extract may be produced by adding the extract to the cosmetic material.

The cosmetic composition may include the *Dahlia pinnata* extract at a content of 16 ng/ml to 20000 ng/ml. In a more preferred example, the cosmetic composition may include the *Dahlia pinnata* extract at a content of 500 ng/ml to 10000 ng/ml. The cosmetic composition including the *Dahlia pinnata* extract has antioxidant activity and has effects such as whitening, anti-aging, and wrinkle improvement.

In this connection, the cosmetic composition may include a cosmetic material that includes various additives of different ingredients depending on the kinds of cosmetics such as cleansing cosmetics, basic cosmetics, color cosmetics, hair cosmetics, and functional cosmetics. The additives that constitute the cosmetic material may also use well-known additives for producing cosmetics. Therefore, detailed descriptions of the cosmetic additive may be omitted.

In an embodiment, the solvent may be ethanol or cosmetic material, but the present disclosure is not limited thereto. The solvent may be embodied as a solvent added to the food.

The *Dahlia pinnata* composition may also be produced in a powders form. The method for producing *Dahlia pinnata* composition powders will be described below with reference to FIG. 2.

Figure 2:
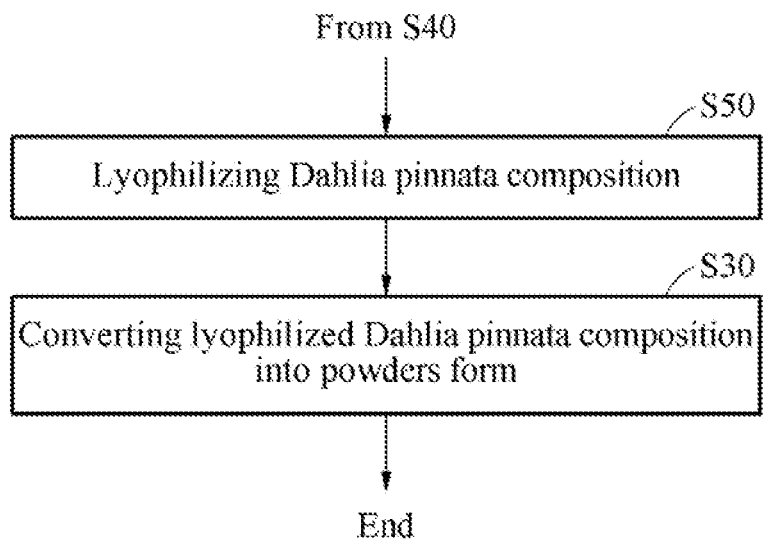
FIG. 2 is a flowchart of the method for producing the *Dahlia pinnata* composition powders according to an embodiment.

FIG. 2 is a flowchart of the method for producing the *Dahlia pinnata* composition powders according to the embodiment.

Referring to FIG. 2, the method for producing powders of the *Dahlia pinnata* composition includes a step (S50) of lyophilizing the *Dahlia pinnata* composition produced by the method for producing the *Dahlia pinnata* composition as described above; and converting the lyophilized *Dahlia pinnata* composition into the powders form (S60).

In the step (S50) of lyophilizing the *Dahlia pinnata* composition, the *Dahlia pinnata* composition is poured into a refrigerator using liquid nitrogen as a refrigerant and rapidly frozen at a temperature below −70° C. The *Dahlia pinnata* composition may be vacuum dried to reduce moisture content therein.

In the step (S60) of converting the lyophilized *Dahlia pinnata* composition into the powders form, the lyophilized *Dahlia pinnata* composition may be added to a cryogenic freezing grinding mill and may be frozen and pulverized in the mill. In the cryogenic freezing mill, liquid nitrogen is injected thereto to attenuate the heat generated during the crushing process. The crushed *Dahlia pinnata* composition has the powders form. The powders-formed *Dahlia pinnata* extract may be added to food and cosmetics.

The *Dahlia pinnata* composition in a liquid or powders form may include the phenolic compounds with an antioxidant efficacy. Further, it has been shown that the *Dahlia pinnata* composition has antioxidant activity to exhibit a high antioxidant effect. The *Dahlia pinnata* flowers have a variety of colors, so that they may be used as natural pigments in food and cosmetics, as well as the antioxidant and anti-aging agent.

Hereinafter, the present disclosure will be described in more detail through Examples. It will be apparent to one of ordinary skill in the art that these Examples are only for the purpose of illustrating the present disclosure more specifically and that the scope of the present disclosure is not limited to these Examples.

EXAMPLES 200 ml of ethanol was added to 20 g of *Dahlia pinnata* petal and stirred at a speed of 30 rpm for 5 hours at a room temperature to extract *Dahlia pinnata* extract. Then, *Dahlia pinnata* composition was prepared by filtering the extract through a 25 mm syringe filter and then controlling the content of the *Dahlia pinnata* extract via adding ethanol as a solvent thereto.

Table 1 shows the contents of the *Dahlia pinnata* extract in the *Dahlia pinnata* composition according to each of Examples.

TABLE 1

| Examples | Dahlia pinnata extract content |
| --- | --- |
| Example 1 | 250 µg/ml |
| Example 2 | 500 µg/ml |
| Example 3 | 1000 µg/ml |
| Example 4 | 10000 µg/ml |
| Example 5 | 20000 µg/ml |
| Example 6 | 0.64 µg/ml |
| Example 7 | 3.2 µg/ml |
| Example 8 | 16 µg/ml |
| Example 9 | 80 µg/ml |
| Example 10 | 400 µg/ml |
| Example 11 | 100000 µg/ml |

Experimental Example 1

In Experimental Example 1, phenol content was measured by Folin Ciocalteau (F-C) Phenolic Content Quantification Assay. The Folin Ciocalteau (F-C) Phenolic content quantification analysis was performed by mixing 200 µl of 7% sodium carbonate (7% $Na_2CO_3$) in 10 µl of each of the *Dahlia pinnata* compositions of Example 1 to Example 11 to form mixtures, and by maintaining the mixtures at a room temperature for 3 minutes, and by dispensing the mixtures together with 10 µl of 1N Folin Ciocalteau reagent (1N FC Reagent), and by maintaining the mixtures with the reagent at a room temperature for 30 minutes, and by measuring absorbances (750 nm) thereof using a microplate reader (Synergy™ HTX and Synergy™ 2 Multi-Mode Readers, BioTek). Gallic acid (Sigma Aldrich, USA) was used as a reference material.

Table 2 is a table showing phenolic contents according to Experimental Example 1 for Examples 1 to 11.

Referring to Table 2, the *Dahlia pinnata* composition of Example 1 to Example 11 will be described with respect to the phenol content as measured by the method of the Experimental Example 1.

TABLE 2

| Examples | Total phenolic content (µg/100 mg) |
| --- | --- |
| Example 1 | 49.8 ± 6.7 |
| Example 2 | |
| Example 3 | |
| Example 4 | |
| Example 5 | |
| Example 6 | |
| Example 7 | |
| Example 8 | |
| Example 9 | |
| Example 10 | |
| Example 11 | |

Example 1 to Example 11 have the total phenolic compound contents relative to the *Dahlia pinnata* extract as measured as from 43.1 µg/100 mg to 56.5 µg/100 mg although the total phenolic compound contents of Example 1 to Example 11 have small differences in accordance with the contents of *Dahlia pinnata* composition. The *Dahlia pinnata* compositions produced according to the Examples may include antioxidant properties because the compositions include the antioxidant phenolic compounds. The phenolic compounds have physiological activity such as anticancer activity in addition to antioxidant effect. Therefore, it could be known that the *Dahlia pinnata* composition may have effects such as antioxidant activity and anticancer activity when the composition is used in foods and cosmetics.

Hereinafter, referring to FIG. 3, the results of measurement of radical removal capabilities by the compositions of Example 1 to Example 5 will be described via a DPPH method.

Comparative Example

L-Ascorbic acid (Sigma Aldrich, 50-81-7, USA) was added to ethanol so that the content of ascorbic acid included in ethanol was 50 µg/ml. Ascorbic acid is an organic compound with antioxidant properties. Ascorbic acid is one of the vitamins C and has a lactone structure. Ascorbic acid is an optically active compound widely used as an antioxidant for food additives.

Experimental Example 2

In Experimental Example 2, DPPH radical removal capability was measured for Example 1 to Example 5. To measure the DPPH radical removal capability, 100 µl of 0.2 mM DPPH solution dissolved in 99.5% methanol was added to 100 µl of each of the compositions of Example 1 to Example 5 and Comparative Example to form mixtures, and, then, in the mixtures, reactions occur at 37° C. for 30 minutes. Then, the absorbances thereof were measured at 517 nm using a microplate reader (Synergy™ HTX and Synergy™ 2 Multi-Mode Readers, BioTek). Then, the DPPH radical removal capability was measured and thus the antioxidant capability was evaluated, and the measurement results in the graph of FIG. 3 were obtained.

Figure 3:
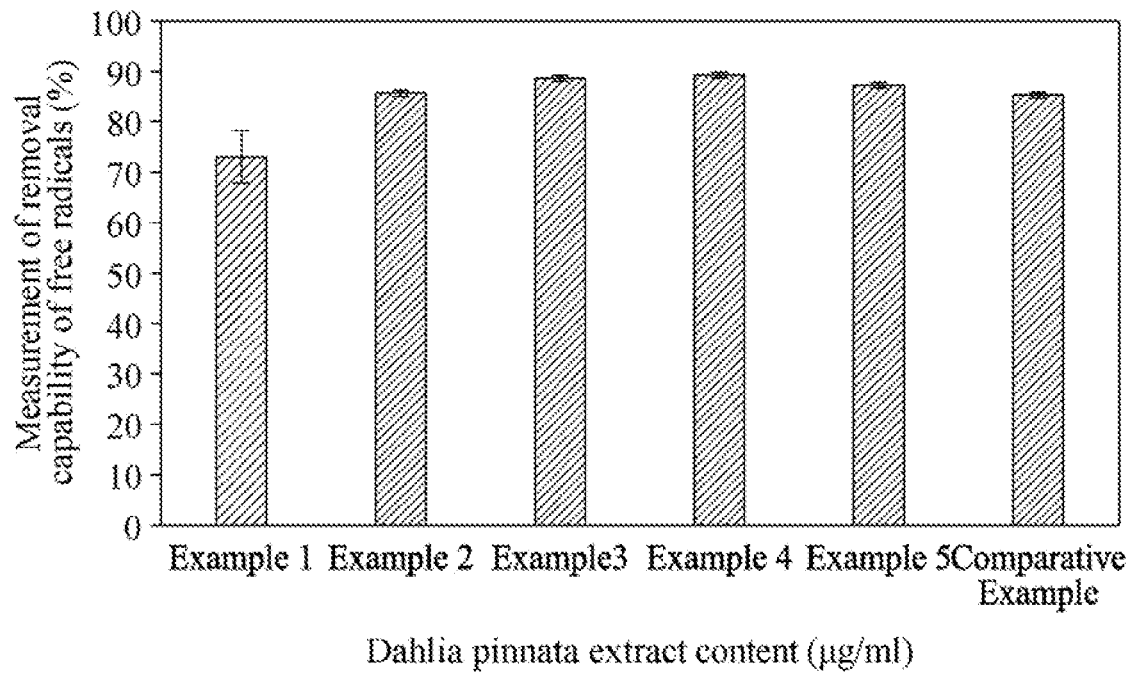
FIG. 3 is a graph of the removal capability of free radical by the *Dahlia pinnata* composition according to an embodiment.

FIG. 3 is a graph of DPPH free radical removal capability measurements of the *Dahlia pinnata* compositions according to an embodiment.

Referring to FIG. 3, the DPPH free radical removal capability of the *Dahlia pinnata* composition of Example 1 is 72.5% to 74.0%; the DPPH free radical removal capability of the *Dahlia pinnata* composition of Example 2 is 85.3% to 86.3%; the DPPH free radical removal capability of the *Dahlia pinnata* composition of Example 3 is 88.07% to 89.07%; the DPPH free radical removal capability of a *Dahlia pinnata* composition of Example 4 is 88.4 to 89.4%; the DPPH free radical removal capability of the *Dahlia pinnata* composition of Example 5 is 86.3% to 87.3%; and the DPPH free radical removal capability of the ascorbic acid of Comparative Example is 84.5% to 85.9%. In other words, the *Dahlia pinnata* composition with a *Dahlia pinnata* extract content exceeding 250 µg/ml could be confirmed to exhibit an antioxidant efficacy similar to the ascorbic acid.

Meanwhile, although not shown, the DPPH free radical removal capability was measured at a content of the range of 5 µg/ml to 20000 µg/ml of the ascorbic acid relative to the solvent. In this measurement, it was confirmed that 81% to 85.9% of the DPPH free radical removal capability was exhibited in a range of a content of 100 µg/ml to 20000 µg/ml of the ascorbic acid relative to the solvent.

Hereinafter, the results of measurement of inhibition of superoxide dismutase (SOD) activity by the *Dahlia pinnata* compositions of Example 6 to Example 10 will be described with reference to FIG. 4.

Experimental Example 3

In Experimental Example 3, the superoxide dismutase kit (SOD Assay Kit-WST) was used to measure the inhibition of superoxide dismutase activity by the *Dahlia pinnata* compositions of Example 6 to Example 10. To this end, each of mixtures between the *Dahlia pinnata* compositions from Examples 6 to 10 and water-soluble tetrazolium salt (WST) solution, superoxide dismutase solution (SOD enzyme solution), buffer solution, dilution water was dispensed into a 96-well plate. The superoxide dismutase (SOD) as an enzyme used in this assay is one of the most important antioxidant enzymes that decomposes superoxide anion ($O_2$) into hydrogen peroxide ($H_2O_2$) and oxygen molecules. The SOD activity inhibition rate was measured based on this mechanism.

200 µl of tetrazolium salt solution and 20 µl of superoxide dismutase solution were added into 20 µl of *Dahlia pinnata* compositions from Example 6 to Example 10 to form samples. 20 µl of deionized distilled water ($ddH_2O$) was added into 200 µl of tetrazolium salt solution and 20 µl of superoxide dismutase solution to form a first blank. 20 µl of the *Dahlia pinnata* compositions were added into 200 µl of tetrazolium salt solution and 20 µl of diluting water to form a second blank. 20 µl of deionized distilled water was added into 200 µl of tetrazolium salt solution and 20 µl of diluting water to form a third blank. 240 µl of each of samples and the first to third blanks was dispensed into a 96-well plate and reacted at 37° C. for 20 minutes. The absorbances thereof were then measured at 450 nm using a microplate reader (Synergy™ HTX and Synergy™ 2 Multi-Mode Readers, BioTek). The values of the absorbances and the inhibition rate of SOD activity (%) by the *Dahlia pinnata* compositions of Example 6 to Example 10 were calculated by a following equation:

Inhibition rate of SOD activity (%)=$\{[(A_{blank1}-A_{blank3})-(A_{sample}-A_{blank2})]/(A_{blank1}-A_{blank3})]\times$ 100, <Equation> where $A_{sample}$ refers to the absorbance value of each sample, $A_{blank1}$ refers to the absorbance value of the first blank,
$A_{blank2}$ refers to the absorbance value of the second blank,
$A_{blank3}$ refers to the absorbance value of the third blank.

Figure 4:
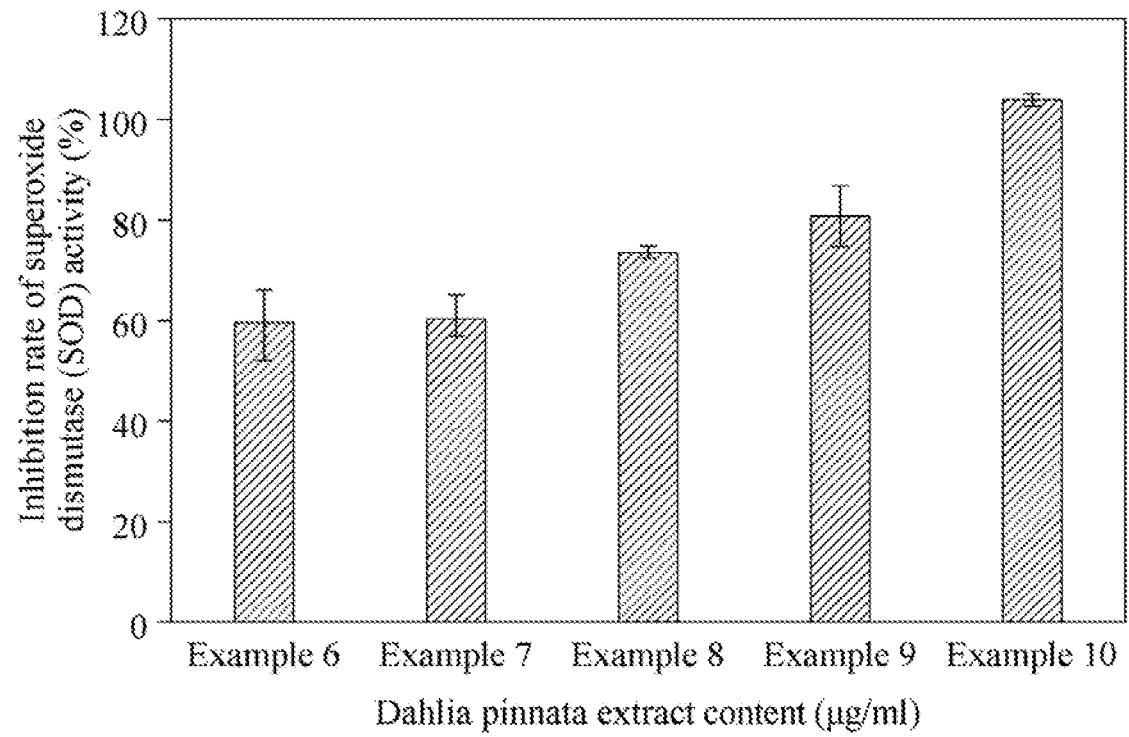
FIG. 4 illustrates an inhibition rate of superoxide dismutase activity by the *Dahlia pinnata* composition according to an embodiment.

FIG. 4 illustrates the inhibition rate of SOD activity by the *Dahlia pinnata* composition according to an embodiment.

As illustrated in FIG. 4, the *Dahlia pinnata* composition of Example 6 had an average inhibition rate of the SOD activity of 59.1%. In *Dahlia pinnata* composition of Example 7, the inhibition rate of SOD activity was measured as 52.7% to 69.1%, and the average inhibition rate thereof was measured as 60.9%. In *Dahlia pinnata* composition of Example 8, the inhibition rate of SOD activity was measured as 71.1% to 76.1% and the average inhibition rate thereof was measured as 73.6%. In *Dahlia pinnata* composition of Example 9, the inhibition rate of SOD activity was measured as 67.8% to 92.7%, and the average inhibition rate thereof was measured as 80.7%. Further, the *Dahlia pinnata* composition of Example 10 showed that the inhibition rate of the SOD activity was as 101.2% to 105.6%, and the average inhibition rate thereof was measured as 103.4%. These measurements could also confirm that the *Dahlia pinnata* compositions effectively inhibited the activity of SOD. The inhibition rate of the activity of SOD by the *Dahlia pinnata* composition could increase by increasing the content of *Dahlia pinnata* extract.

Referring to the experimental results of Experimental Example 2 and Experimental Example 3, the *Dahlia pinnata* extract contents in the *Dahlia pinnata* compositions is preferably in a range between 16 µg/ml to 20000 µg/ml. It was confirmed that the inhibition rates of SOD activity by the *Dahlia pinnata* compositions smaller than 70% when the content of *Dahlia pinnata* extract is 16 µg/ml or less, whereas the content of the extract exceeding 20000 µg/ml may reduce the DPPH free radical removal capability.

Referring to the graphs of FIG. 3 and FIG. 4, when the *Dahlia pinnata* extract content in the *Dahlia pinnata* composition exceeded 10000 µg/ml, the DPPH free radical removal capability decreased. Further, the graphs could confirm that the DPPH free radical removal capability by the *Dahlia pinnata* composition was 80% or more when the *Dahlia pinnata* extract content was greater than 250 µg/ml. Further, the inhibition rate of the SOD activity by the *Dahlia pinnata* composition increased as the extract content increased. When the *Dahlia pinnata* extract content was smaller than 400 µg/ml, the inhibitory rate of SOD activity was reduced to 100% or less. It may be understood that the

*Dahlia pinnata* composition preferably has a content of *Dahlia pinnata* extract of 500 μg/ml to 10000 μg/ml.

With reference to the above experimental results, the cosmetic composition including the *Dahlia pinnata* extract preferably includes the *Dahlia pinnata* extract at a content of 16 μg/ml to 20000 μg/ml relative to the cosmetic composition. More preferably, the content of the *Dahlia pinnata* extract relative to the cosmetic composition is preferably in a range of 500 μg/ml to 10000 μg/ml.

The above experiments have shown that the *Dahlia pinnata* composition extracted from the *Dahlia pinnata* petal has an antioxidant effect. These *Dahlia pinnata* compositions are produced in the form of liquids or powders which are easily added to a variety of foods and cosmetics requiring an antioxidant efficacy.

Although the present disclosure has been described with reference to the above-described embodiments, various modifications and changes may be made thereto by those skilled in the art. For example, although the method steps as described are performed in a different order than the described step order or components such as structures, devices, and/or elements as described are combined or coupled in different forms or are substituted or replaced with other components or equivalents than the described components, appropriate results may be achieved.

The invention claimed is:

1. A cosmetic composition having antioxidant efficacy, the cosmetic composition comprising an extract of *Dahlia pinnata*,
   (i) wherein the composition has a content of the *Dahlia pinnata* extract in a range of from 500 μg/ml to 10000 μg/ml,
   (ii) wherein the *Dahlia pinnata* is extracted by adding ethanol to petals of *Dahlia pinnata* at a ratio of 5 to 20 ml of ethanol per 1 g of petals and stirring the mixture,
   (iii) wherein the cosmetic composition comprises the extract of (ii), and
   (iv) wherein the composition has a phenolic compound content of 43.1 μg/100 mg to 56.5 μg/100 mg.

2. A method for producing a composition comprising an extract of *Dahlia pinnata*, the method comprising:
   (a) obtaining *Dahlia pinnata* petals;
   (b) adding ethanol to the *Dahlia pinnata* petals at a ratio of 5-20 ml of ethanol per 1 g of petals, and stirring the mixture, to obtain an extract of *Dahlia pinnata*, wherein the extract has a content of phenolic compounds of 43.1-56.5 μg/100 mg;
   (c) filtering the extract made in step (b); and
   (d) diluting the extract made in step (c) with a solvent, to obtain a composition that has antioxidant efficacy, wherein the extract made in step (c) is diluted at a ratio of 500 μg/ml to 10,000 μg/ml.

3. The method of claim 2, wherein in step (c), the extract is filtered through a filter attached to a syringe.

4. A composition comprising an extract of *Dahlia pinnata* that is made by the method of claim 2, wherein the composition has antioxidant efficacy.

5. A method for producing a powdered composition comprising an extract of *Dahlia pinnata*, comprising the steps of:
   (a) lyophilizing the composition made by the method of claim 2; and
   (b) making a powder from the lyophilized composition made in step (a).

6. A cosmetic composition comprising the powdered composition made by the method of claim 5, wherein the cosmetic composition has antioxidant efficacy.

7. A cosmetic composition comprising the composition made by the method of claim 2, wherein the cosmetic composition has antioxidant efficacy.

8. The method of claim 2, wherein, when the composition made by the method of claim 2 tested in an assay for antioxidant activity that measures the degree to which 2,2-diphenyl-1-picrylhydrazyl (DPPH) free radicals are removed, the composition comprising the *Dahlia pinnata* extract removes 85-89% of the DPPH free radicals.

* * * * *